United States Patent [19]

Schmidt et al.

[11] Patent Number: 4,500,653

[45] Date of Patent: Feb. 19, 1985

[54] BLOWING AGENTS FOR THERMOPLASTIC COMPOSITIONS

[75] Inventors: Manfred Schmidt; Mark W. Witman, both of Krefeld, Fed. Rep. of Germany; Gerard E. Reinert, McMurray; In C. Lim, Pittsburgh, both of Pa.

[73] Assignee: Mobay Chemical Corporation, Pittsburgh, Pa.

[21] Appl. No.: 531,982

[22] Filed: Sep. 14, 1983

[51] Int. Cl.³ ............................................. C08J 9/10
[52] U.S. Cl. .................................... 521/90; 521/180; 521/182; 521/184
[58] Field of Search ................. 521/90, 180, 182, 184

[56] References Cited

U.S. PATENT DOCUMENTS

| | | | |
|---|---|---|---|
| 3,779,954 | 12/1973 | Wirth et al. | 260/2.5 R |
| 3,781,233 | 12/1973 | Mueller et al. | 260/2.5 R |
| 4,097,425 | 6/1978 | Niznik | 260/2.5 N |
| 4,163,037 | 7/1979 | Niznik | 264/54 |
| 4,263,409 | 4/1981 | Liberti | 521/81 |
| 4,288,560 | 9/1981 | Kirchmayr et al. | 521/90 |
| 4,334,030 | 6/1982 | Kochanowski | 521/90 |
| 4,406,846 | 9/1983 | Paschke et al. | 521/90 |

OTHER PUBLICATIONS

Tett. Lett., (44), pp. 3875–3878, (1974).

*Primary Examiner*—Morton Foelak
*Attorney, Agent, or Firm*—Gene Harsh; Lawrence S. Pope; Aron Preis

[57] ABSTRACT

The present invention is directed to derivatives of azoles, their preparation and their use as chemical blowing agents for thermoplastic molding compositions. The agents of the invention are characterized in their improved compatibility with the resin wherein they are incorporated.

12 Claims, No Drawings

BLOWING AGENTS FOR THERMOPLASTIC COMPOSITIONS

FIELD OF THE INVENTION

The present invention is directed to chemical blowing agents and more particularly to certain derivatives of azoles useful in the foaming of thermoplastics.

BRIEF DESCRIPTION OF THE INVENTION

The invention is directed to derivatives of azoles, their preparation and use as chemical blowing agents for thermoplastics. The chemical blowing agents of the invention are characterized in their improved compatibility with the resin upon foaming.

BACKGROUND OF THE INVENTION

The present invention is based on the discovery that certain oxadiazolone compounds, some of which are described in *Tett. Lett.* (44) pp. 3875–3878 (1974), can be employed as foaming agents in high temperature thermoplastic polymers such as polycarbonate, polysulfone and the like. Other blowing agents, such as 5-phenyltetrazol and benzamides (U.S. Pat. No. 3,781,233 and U.S. Pat. No. 3,779,954) and dioxazolones (U.S. Pat. No. 4,288,560) although effective foaming agents for polycarbonate, cause degradation of the resin during the foaming process. The principal technical advantage of the present oxadiazolone derivatives is, therefore, the fact that less degradation of the resin results during foaming.

The art is noted to include U.S. Pat. Nos. 4,097,425 and 4,163,037 which disclose dihydrooxadiazinones as chemical blowing agents, as well as U.S. Pat. No. 4,263,409 which discloses chemical containing decomposable groups such as azo, N-nitroso, carboxylate, carbonate, heterocyclic nitrogen containing and sulfonyl hydrazide groups, as suitable foaming agents.

The azole derivatives of the present invention are noted for their improved compatibility with the resin upon foaming as expressed in the virtual elimination of resin degradation.

DETAILED DESCRIPTION OF THE INVENTION

According to the present invention there are provided compounds characterized in that their molecular structure entails at least one pentatomic heterocyclic ring conforming to

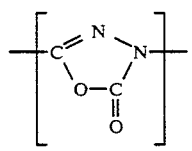

which compounds are particularly suitable as chemical blowing agents.

Further in accordance with the invention there are provided injection moldable blends comprising a thermoplastic resin and about 0.1 to about 25 percent, relative to the weight of said blend, of said chemical blowing agent.

Also provided in accordance with the invention is a blowing agent concentrate comprising a thermoplastic resin and a sufficient amount of said agent.

Among the compounds suitable as chemical blowing agents in the present context are compounds having the formula

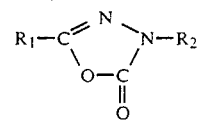

wherein $R_1$ is a $C_6$–$C_{16}$ aryl, a $C_1$–$C_{32}$ alkyl, or a $C_2$–$C_{12}$ alkenyl, and $R_2$ is a $C_1$–$C_{20}$ alkyl, $C_7$–$C_{20}$ alkylaryl, trialkylsilyl, a hydrogen atom, an alkali metal or

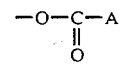

where A is $C_1$–$C_{12}$ alkyl or $C_6$–$C_{16}$ aryl, or

wherein B is a $C_1$–$C_{18}$ alkyl or a $C_6$–$C_{16}$ aryl.

Further among the compounds suitable are the ones conforming to

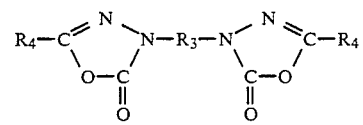

wherein $R_4$ independently denotes a $C_6$–$C_{16}$ aryl, a $C_1$–$C_{32}$ alkyl or a $C_2$–$C_{12}$ alkenyl $R_3$ denotes a $C_2$–$C_{18}$ alkyl, $>C=O$, a dialkylsilyl,

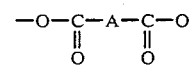

where A is a $C_1$–$C_{20}$ alkyl or a $C_6$–$C_{16}$ aryl, or

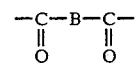

where B is a single bond, $C_6$–$C_{20}$ aryl or a $C_1$–$C_{20}$ alkyl.

Further suitable are compounds conforming to

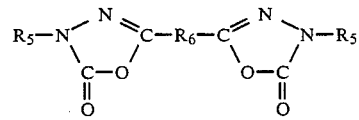

wherein $R_5$ independently denotes $C_1$–$C_8$ alkyl, $C_7$–$C_{18}$ alkylaryl, a hydrogen atom or an alkali metal, or

where B is a $C_1$–$C_{18}$ alkyl or a $C_6$–$C_{16}$ aryl, or

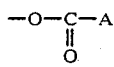

where A is $C_1-C_{12}$ alkyl or a $C_6-C_{16}$ aryl and $R_6$ denotes a single bond, a $C_1-C_{12}$ alkyl or $C_6-C_{16}$ aryl.

The preparation of compositions suitable in the present practice as chemical blowing agents may be carried out by the phosgenation of acid hydrazides, the reaction is preferably carried out in any suitable solvent such as any of $CH_2Cl_2$, MCB, toluene, xylene, water, acetone, $CHCl_3$ and tetrachloroethane or mixtures thereof. In an alternative route, where alkali salts of the oxadiazolone are reacted with organo halides, the solvent is preferably aprotic or polar such as acetonitrile, DMF, acetone or glycol dimethylether; suitable catalysts for the reaction include triphenyl phosphine, or a tertiary amine such as triethyl amine present at an amount of 0.05 to about 5 percent relative to the weight of the salt. A yet additional synthesis route entails a reaction of organo halides (Hal-R-Hal) with alkali salts of oxadiazolone.

The following examples are intended to illustrate in more detail the preferred embodiments of the invention.

EXAMPLES

Example 1

The following 2-phenyl-4-ethyl-1,3,4-oxadiazolone-(5) was prepared by reacting 100 gms (0.5 mole) of the potassium salt of 2-phenyl-1,3, 4-oxadiazolone-(5), with 54.5 gm (0.5 moles) of ethyl bromide (b.p. 38° C.), in 400 ml of acetonitrile, at about 30°-35° C. for 1 hour. Further, 10.9 gms (0.1 mole) of ethyl bromide were added to the reaction (6 hours, 82° C., reflux). The reaction product was filtered and the filtrate evaporated and the residue was recrystallized from an ethanol solution. The product conforming to

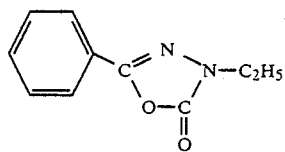
(Ia)

is characterized in that its melting point was determined to be 46° C. and its decomposition temperature was 240° C. Its gas yield is indicated to be about 236 ml/gm.

(Ia) In still a different synthesis route, 68 gms (0.5 moles) of benzhydrazide, 101 gms (1 mole) of triethylamine, and 1 liter of methylene chloride were charged to a 2 liter flask. Liquified phosgene (49.5 gms, 0.5 mole) was then bubbled in. The reaction temperature was kept below 40° C. A nitrogen purge followed the completion of the reaction. The product was filtered and washed with water and then with methylene chloride. The solid is then recrystallized from water. The product, 2-phenyl-1,3,4-oxadiazolone-(5) is characterized in that its melt temperature is about 137°-139° C.

(Ib) Additionally prepared was 2-phenyl-4-benzyl-1,3,4-oxadiazolone-(5). The preparation procedure was as follows:

64.5 gm (0.402 moles) of 2-phenyl-1,3,4-oxadiazolone-(5) prepared as above were dissolved in hot ethanol (600 ml) and potassium hydroxide (22.6 gms, 0.402 moles) added. After cooling the precipitate was filtered and washed with ethanol and then with hexane. The product, potassium-2-phenyl-1,3,4-oxadiazolone-(5) (82 gms/0.41 moles) was dissolved in methanol and introduced into a three-necked flask and kept at a maximum of 20° C. Benzylchloride solution in methanol was then introduced dropwise. The yield was 51% and the material had a melt point of 117°-118° C.

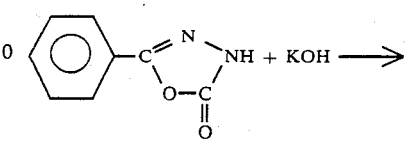

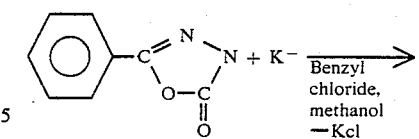

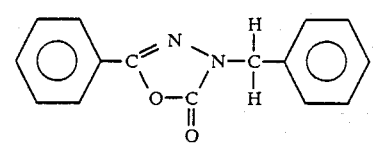

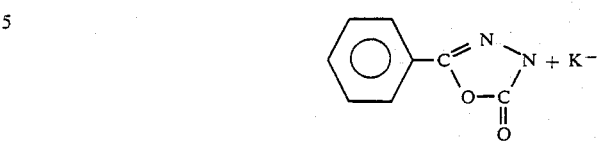

(Ic) A higher yield was realized upon a synthesis route as follows:

85.4 g (0.527 mole) of the oxadiazolone were dissolved in ethanol (1 liter) and ethanol in KOH (29.52 gm, 0.527 mole KOH) was added. The resulting powder/solution was cooled and filtered (yield 87.2 gm; 0.436 mole, 87% of theory).

To that potassium salt (72.7 gm; 0.3635 mole) was added 46.94 gm of benzylchloride and 400 ml of acetonitrile. After the reaction (1 hr. at 60° C. and 1 hr. at 82° C.) reflux +0.5 gm triphenyl phosphine after ½ hour, potassium chloride was filtered off and the filtrate evaporated. The residue was recrystallized from isopropanol. The total yield was 82.5 gr; 90.0% of theory, and the product was characterized by its melting point 118°-119° C. and decomposition temperature 230° C. The product was characterized in its structure

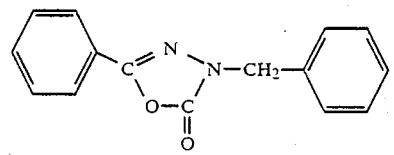
(Ib)

The thermal properties were determined in a sealed bomb and the experimental conditions and test results are tabulated below.

| Experimental starting conditions | |
|---|---|
| titanium bomb: | weight - 8.206 gm |
| | empty volume - 9.1 ml |
| sample weight: | 1.6915 gm (sealed with $N_2$ at 14.7 psia) |

| | Experimental starting conditions | |
|---|---|---|
| phi factor: | 2.26 | |
| Initial Decomposition: | 230° C. (0.02° C./min, 46 psia, 0.05 psia/min) | |
| Decomposition: | 240° C.: 0.44° C./min, 58 psia, 0.09 psia/min) | |
| Programmed final temp.: | 300° C. (1° C./min, 184 psia, 4.20 psia/min) | |
| Cooling down temp.: | 25° C. (77.5 psia) | |

(Id) The preparation of 2-phenyl-4-benzhydryl-1,3,4-oxadiazolone-(5) entailed a catalyzed (0.1 gm of triphenyl phosphine) reaction of 94.42 gm (0.472 moles) of the potassium salt of 2-phenyl-1,3,4-oxadiazolone-(5) with 93.2 gm (0.460 moles) of diphenylmethyl chloride (=benzhydrylchloride), in 400 ml of ethylene glycoldimethyl ether solution. The reaction was carried out for 3 hours at about 80°–100° C. The yield was about 56.4% of theory and the product was characterized in that its melt temperature was at about 149°–150° C. and that the decomposition was at about 260° C.

(Ie) Also prepared from the potassium salt of 2-phenyl-1,3,4-oxadiazolone-(5) upon a reaction with acetonitrile (triphenyl phosphine as a catalyst) was 2-phenyl-4-acetyl-1,3,4-oxadiazolone-(5) conforming structurally to

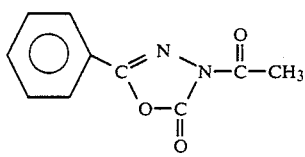

The compound was characterized by its melting temperature of about 113°–115° C. and in that its decomposition temperature was about 200° C.

Example 2

The preparation of N,N'-bis(2-phenyl-1,3,4-oxadiazolone-(5)-urea

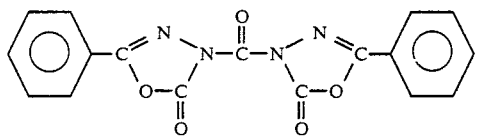 (I)

may be carried out by either of the following routes:

(i) from 2-phenyl-1,3,4-oxadiazolone-(5) potassium salt:

Into a 1 liter flask were charged 2-phenyl-1,3,4-oxadiazolone-(5) potassium salt (16.2 gm, 0.1 mole), triethylamine (15.1 gm, 0.15 mole) and 200 ml of methylene chloride solvent. Phosgene (5.0 gm, 0.05 mole) was bubbled through the solution while holding the temperature at 5° C. Triethylamine hydrochloride formed during the reaction was filtered and the bis-urea isolated by evaporating the solvent. Recrystallization of the white crystalline solid afforded 14.0 g (80% yield) of the purified product (MP (dec.) 247°–248° C.).

The product was analyzed and was found to contain the following (%):

| | Theoretical | Actual |
|---|---|---|
| C | 58.28 | 58.21 |
| H | 2.86 | 3.07 |
| N | 16.00 | 15.89 |
| O | 22.86 | 22.45 |

(ii) from 2-phenyl-1,3,4-oxadiazolone-(5):

Into a 1 liter flask with a K-head adaptor, condenser and gas inlet tube was charged 500 ml of methylene chloride solvent, 40.5 gm (0.25 mole) of 2-phenyl-1,3,4-oxadiazolone-(5) and (25.5 gm, 0.25 mole) triethylamine. While holding the temperature at 0.5° C. phosgene (12.3 gm, 0.125 mole) was bubbled through the solution over a period of 20 min. The solution was then refluxed for one hour. After purging the remaining phosgene from the solution with $N_2$ the methylene chloride was evaporated. The white solid remaining was washed several times with water and dried. The product was recrystallized from chlorobenzene. Yield: 37.5 g, 87.7% yield, mp dec. 240° C.

Example 3

The preparation of 4,4'-diphenoxycarbonyl-bis-$\alpha,\beta$-(1,3,4-oxadiazolone-[5]-yl)ethane (=DBOE) conforming to

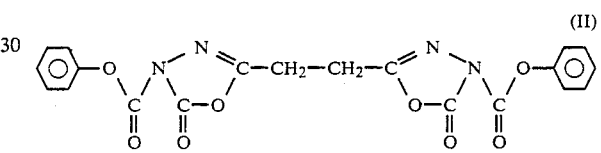 (II)

was carried out as follows:

500 gms (5.05 mole) of phosgene were added within 3½ hours to a well stirred solution—maintained at 10° C.—of 365.5 gm (2.5 mole) of succinic acid dihydrazide while keeping the pH at 3 to 3.5 by adding simultaneously a 40 wt. percent solution of aqueous sodium hydroxide. Nitrogen is then bubbled through the well stirred reaction mixture for 30 mins. at room temperature. The precipitate (ethylenebis-oxadiazolone) is isolated by filtration, washed with water until it is chloride-free and then dried at 90°–100° C. in vacuum.

The reaction yielded 456 gms (=92% of theory), mp 225°–226°. The elemental analysis corresponds well with the theory (C=36.10%, H=3.04%, N=28.40%; compared to the theoretical values 36.36%, 3.03% and 28.28%, respectively).

166.4 g (0.84 mole) ethylenebisoxadiazolone, 600 ml isopropanol and a solution of 94.13 g (1.68 mole) potassium hydroxide in 150 ml isopropanol are stirred for ½ hour at room temperature. After adding 0.2 gm triethylamine, a solution of 262.92 g (1.68 mole) phenylchloroformate in 250 ml acetone is added while keeping the temperature at 20°–25° C. by cooling. The well stirred reaction mixture is then warmed up to 30° C. for 1½ hours and boiled under reflux for additional 15 minutes. The precipitate is isolated by filtration, washed with water until it is chloride-free and dried at 100° C. in vacuum.

The yield was 296.2 gm (80.5% of theory, recrystallized from monochlorobenzene) and the product was characterized in that its melting temperature was 193°–194° C. and in that its decomposition temperature was about 280°–285° C. The chemical analysis indicated 54.60% carbon, 3.09% hydrogen and 12.86% nitrogen (compared with the theoretical 54.79%, 3.29% and 12.79%, respectively).

Example 4

The preparation of di-(2-phenyl-1,3,4-oxadiazolone-[5])-4-terephthalamide (hereinafter DPOT) conforming to

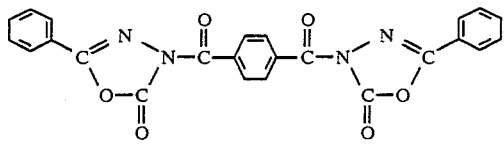
(III)

was carried out as follows:

50 g (0.368 mole) benzhydrazide (mp 116° C.) are stirred in 300 ml acetone. Into this suspension is bubbled 41.8 gm (0.438 mole) of phosgene while keeping the temperature at 10°–20° C. and holding the pH-value of the stirred reaction mixture at 2 to 2.5 by adding simultaneously a 45% aqueous solution of sodium hydroxide (ca. 70 ml). The reaction mixture is stirred for another ½ hour at 20° C. The precipitate is isolated, washed with water and dried at 100° C. in vacuum. The product, 2-phenyl-1,3,4-oxadiazolone-(5), is reacted in 400 ml of water and a sufficient amount of sodium hydroxide to maintain a pH of 10 with 37.84 gms (0.184 moles) of terephthalic acid dichloride in the presence of 0.014 gm of triethylamine to yield a colorless precipitate. The product was dried at 80° to 100° C. in vacuum.

The yield was 78 gms (93% of theory) and the product was characterized in that its melt temperature was about 282° C. and in that its decomposition temperature was at about 285° C. The product is insoluble in alcohols, acetone, dioxane, ethylacetate, or halogenated hydrocarbons. The elemental analysis indicates 63.20% carbon, 3.10% hydrogen and 12.30% nitrogen; compared to the theoretical values of 63.40%, 3.08% and 12.33%, respectively.

Example 5

Preparation of 2-phenyl-4-isopropyloxycarbonyl-1,3,4-oxadiazolone-(5).

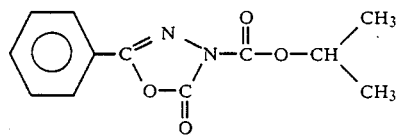

100 grams (0.736 mol) of benzhydrazide was suspended in 600 ml of acetone with stirring. While maintaining the reaction at 10°–20° C., phosgene (93.6 g, 0.976 mol) was added. Approximately 140 ml of 45% aqueous NaOH was added simultaneously to hold the pH between 2–2.5. The product was isolated, washed with water and dried at 100° C. The product, 2-phenyl-1,3,4-oxadiazolone-(5) is reacted in 500 ml of an acetone/water mixture (20% water) at pH-10 in the presence of triethylamine with 0.74 mol of isopropylchloroformate to yield (71%) of a white crystalline product of the following constituents: 57.8% carbon, 5.37% hydrogen and 11.6% nitrogen, (compared with the corresponding theoretical values 58.6, 4.84 and 11.30).

A blend of 0.2% of the oxadiazolone of the Examples and a bisphenol-A based polycarbonate (Rel. viscosity 1.298 in a 0.5 wt. % $CH_2CL_2$ solution) was heated for 30 min. at 300° C. in vacuo. The relative viscosity of the polycarbonate after heating was 1.289 compared to 1.273 for a similar blend containing 0.2% Expandex 5PT (5-phenyl-tetrazol).

Example 6

Preparation of 1,3-bis-2,2'-[4,4'-diisopropyloxycarbonyl-1,3,4-oxadiazolone-(5)] benzene.

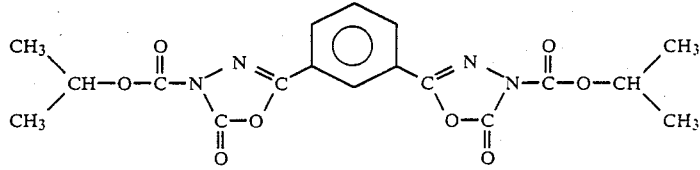

Isophthalic Hydrazide (100 g, 0.515 mol) was suspended in 300 ml of acetone with stirring. While holding the reaction temperature at (10°–20° C.) phosgene (121.3 g, 1.23 mol) was added. Sodium Hydroxide (45% in $H_2O$, 175 ml) was added to hold the pH in the range of 2.0–2.5. Following the phosgene addition the product was isolated and dried at 100° C.

This product 1,3-bis-2,2'[1,3,4-oxadiazolone-(5)] benzene was suspended in 500 ml of an acetone/water mixture (20% water) at pH-10 and reacted with isopropylchloroformate (126.2 g, 1.03 mol) in the presence of triethylamine catalyst. The product was recovered from solution as a white crystalline product in 80% yield.

The oxadiazolone of the example was blended with a polycarbonate resin similar to that of Example 5. A relative viscosity of 1.285 was observed after heating at 300° C. for 30 min. in comparison to 1.273 obtained for a blend containing the same polycarbonate resin and Expandex 5PT.

The chemical blowing agent of the invention is blended with a thermoplastic resin in an extruder and the extrudate comminuted into suitable pellets. The amount of added chemical blowing agent is generally about 0.1 to about 25 percent, with concentrates generally containing the higher amounts of the chemical blowing agents, preferably 3 to 25% and molding composition generally containing the lower end of the range, preferably 0.1 to 1.0%, the percents being relative to the total weight of the chemical blowing agent and thermoplastic resin. In the embodiments whereby the chemical blowing agent is used as a component of a concentrate, it is contemplated that the following are the operational variations:

(a) a powder blend of thermoplastic resin and oxadiazolone blowing agent, (b) thermoplastic granulate pellets coated with oxadiazolone blowing agent, or thermoplastic resin/oxadiazolone powder blend, (c) an encapsulated oxadiazolone blowing agent concentrate.

Preferably the thermoplastic resins suitable in the context of the invention are polysulfone, polyether sulfone, polyester, polycarbonate, polyestercarbonate, aromatic polyester, including such as are based on bisphenol A and aromatic acids, thermotropic liquid crystalline resins, polyamide, polyetherimide, polyphenyleneoxide, ABS resins and mixtures thereof. Most preferred are polycarbonate, polyalkylene terephthalate, aromatic polyester carbonates and aromatic polyesters. The resins listed above as suitable and as preferred are known in the art and are preparable by known methods or are readily available in commerce.

The blends comprising the chemical blowing agent of the invention and a thermoplastic resin may further contain any of flame retarding agents, impact modifiers, glass fibers and/or fillers of various types as well as stabilizers and release agents as are known in the art.

The Examples below demonstrate the properties of blends in accordance with the invention and describe their properties.

Example 7

Melt stability

Compound (I) above was blended with Merlon M-50 (a bisphenol-A based homopolycarbonate characterized in that its melt flow index per ASTM D-1238 is about 3.0–5.9 gm/10 min.) in powder form, in amounts of 0.2–1.0 percent by weight. The powder blends were aged in vacuo at 300° C. for a period of 30 min. The relative viscosities of the blends after aging at 300° C. for 30 minutes were determined. In comparison to a prior art blowing agent (5-phenyl-tetrazol) the novel compositions of the invention are significantly more stable in that less polymer degradation was indicated. See Table 1.

TABLE 1

| | Melt Stability Comparisons | | |
|---|---|---|---|
| | Concentration of blowing agent in polycarbonate | Blowing Agent of the invention | Prior Art agent |
| Trial #1 | 0.0 | 1.300 | 1.300 |
| | 0.2 | 1.311 | 1.284 |
| | 0.5 | 1.300 | 1.261 |
| | 1.0 | 1.292 | — |
| Trial #2 | 0.0 | 1.311 | 1.311 |
| | 0.2 | 1.293 | 1.276 |
| | 0.4 | 1.288 | 1.262 |

Examples 8–9

Compound (I) above was tumble blended into hot (70°–80° C.) pellets of Merlon SF-800 available from Mobay Chemical Corporation—a product containing essentially a bisphenol-A based homopolycarbonate, glass fibers, a flame retardant and a stabilizer. The composition was injection molded into 4 in. diameter discs having a thickness of 0.250 in., using a Newbury 4 oz. injection molding machine. The melt temperature was held constant at 590° C. A maximum density reduction of 25.0 and 38.7% (0.2 and 0.4% blowing agent, respectively) was achieved. The impact strength of the foamed polycarbonate disc at a 27% density reduction was determined using the standard Gardner impact test. The results (see table) show an improvement in impact strength relative to 5-phenyl-tetrazol (Expandex OX-5-PT), a prior art agent.

| | Control Ox 5 PT | 8 | 9 |
|---|---|---|---|
| Added blowing agent, % | 0.2 | 0.2 | 0.4 |
| Maximum density reduction | 37.7 | 25.0 | 38.7 |
| Gardner impact strength (27% density reduction) | 18.6 | — | 24.6 |

Example 10

A master batch concentrate consisting of 95 wt. % of a bisphenol-A based homopolycarbonate having a weight average molecular weight of 24,000 and 5 wt. % of DBOE is made on a Reifenhäuser BT 93 twin screw extruder at 220°–240° C.

A structure-foamed round disc (diameter: 20 cm, thickness: 0.8 mm) from a blend consisting of 85 wt. % of polycarbonate ($\overline{M}w$ = 28,500), 5 wt. % of glass fibers and 10 wt. % of the DBOE-master batch is foamed at 280°–300° C. on an Anker A46 single screw extruder, resulting in density reduction of 30.5%, RV 1,279, impact strength (DIN 53453 = ISO R179): 40.5 kJ/m². The foamed disc had a homogeneous surface and showed no discoloration.

Example 11

A master batch consisting of 95 percent by weight of a bisphenol-A based homopolycarbonate (weight average molecular weight 24,000—as measured by light scattering in dioxane) and 5 percent by weight of DPOT is prepared by coextrusion (twin-screw extruder—Reifenhäuser—at 220°–240° C.). Using 10 wt % of the master batch, 5 wt. % glass fiber and 85 wt. % of a bisphenol-A based homopolycarbonate having a molecular weight (Mw) = 28,500 (RV = 1.290, as measured in a 0.5 wt. % solution in dichloromethane at 25° C.) a round disc with a diameter of 20 cm (thickness: 0.8 cm) is foamed using an injection molding machine (type: Anker A 46) at 290°–310° C.

Density reduction: 28%

RV: 1,280 impact strength (according to DIN 53453 = ISO R 179): 42 kJ/m².

The foamed disc showed no discoloration and had a homogeneous surface.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A molding composition comprising (a) a thermoplastic resin and (b) about 0.1 to about 25% relative to the weight of said (a) plus (b) of a chemical blowing agent characterized in that its molecular structure contains at least one pentatomic heterocyclic ring and conforms to

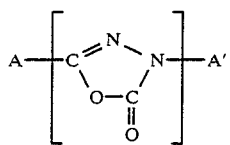

wherein A and A' are moieties which do not negate the foaming ability of said (b) and which do not contribute to the degradation of said (a) upon foaming.

2. The composition of claim 1 wherein said (a) is a polycarbonate.

3. The composition of claim 2 wherein polycarbonate is a homopolycarbonate based on bisphenol A.

4. The composition of claim 1 wherein said (a) is polyalkylene terephthalate.

5. The composition of claim 4 wherein said polyalkylene terephthalate is polyethylene terephthalate.

6. The composition of claim 1 wherein said (b) is selected from the group consisting of compounds having the formula

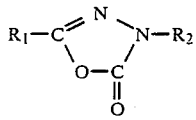

wherein
$R_1$ is a $C_6$–$C_{16}$ aryl, a $C_1$–$C_{32}$ alkyl, or a $C_2$–$C_{12}$ alkenyl, and
$R_2$ is a $C_1$–$C_{20}$ alkyl, $C_7$–$C_{20}$ alkaryl, trialkylsilyl, a hydrogen atom, an alkali metal or

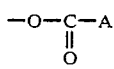

where A is $C_1$–$C_{12}$ alkyl or $C_6$–$C_{16}$ aryl, or

wherein B is a $C_1$–$C_{18}$ alkyl or a $C_6$–$C_{16}$ aryl, and those conforming to

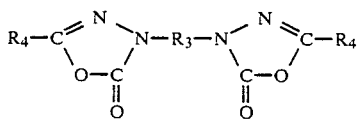

wherein
$R_4$ independently denotes a $C_6$–$C_{16}$ aryl, a $C_2$–$C_{12}$ alkenyl or a $C_1$–$C_{32}$ alkyl and
$R_3$ denotes a $C_2$–$C_{18}$ alkyl, >C=O, a dialkylsilyl,

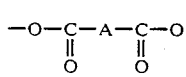

where A is a $C_1$–$C_{20}$ alkyl or a $C_6$–$C_{16}$ aryl, or a

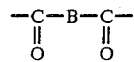

where B is a single bond, $C_6$–$C_{20}$ aryl or a $C_1$–$C_{20}$ alkyl, and those conforming to

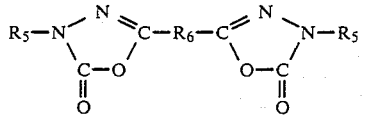

wherein
$R_5$ independently denotes a $C_1$–$C_8$ alkyl, $C_7$–$C_{18}$ alkaryl, a hydrogen atom or an alkali metal, or

where B is a $C_1$–$C_{18}$ alkyl or a $C_6$–$C_{16}$ aryl, or

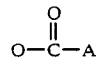

where A is a $C_1$–$C_{12}$ alkyl or a $C_6$–$C_{16}$ aryl and $R_6$ denotes a single bond, a $C_1$–$C_{12}$-alkyl or $C_6$–$C_{16}$ aryl.

7. A molding composition comprising (a) a bisphenol A based homopolycarbonate and (b) di-(2-phenyl-1,3,4-oxadiazolone-[5])-4-terephthalamide.

8. A molding composition comprising (a) a bisphenol A based homopolycarbonate and (b) N,N'-bis(2-phenyl-1,3,4-oxadiazolone-(5))-urea.

9. The composition of claim 7 further comprising glass fibers.

10. A molding composition comprising (a) a bisphenol A based homopolycarbonate and (b) 4,4'-diphenoxycarbonyl-bis-alpha,beta-(1,3,4-oxadiazolone-[5]-yl)ethane.

11. The molding composition of claim 1 wherein said thermoplastic resin is selected from the group consisting of aromatic polyester, aromatic polyester carbonates and thermotropic liquid crystalline resins.

12. A molding composition comprising (a) a polycarbonate resin and (b) about 0.1 to about 25% relative to the weight of said (a) plus (b) of a chemical blowing agent selected from the group consisting of compounds conforming to

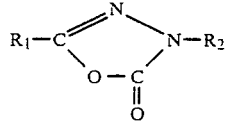

wherein
$R_1$ is a $C_6$–$C_{16}$ aryl, a $C_1$–$C_{32}$ alkyl, or a $C_2$–$C_{12}$ alkenyl, and
$R_2$ is a $C_1$–$C_{20}$ alkyl, $C_7$–$C_{20}$ alkaryl, trialkylsilyl, a hydrogen atom, an alkali metal or

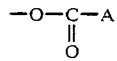

where A is $C_1$-$C_{12}$ alkykl or $C_6$-$C_{16}$ aryl, or

wherein B is a $C_1$-$C_{18}$ alkyl or a $C_6$-$C_{16}$ aryl, and those conforming to

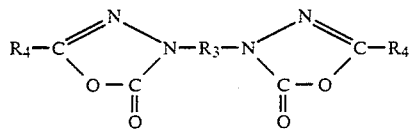

wherein
$R_4$ independently denotes a $C_6$-$C_{16}$ aryl, a $C_2$-$C_{12}$ alkenyl or
a $C_1$-$C_{32}$ alkyl and
$R_3$ denotes a $C_2$-$C_{18}$ alkyl, $$>C=O,$$

a dialkylsilyl,

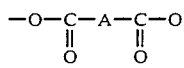

where A is a $C_1$-$C_{20}$ alkyl or a $C_6$-$C_{16}$ aryl, or a

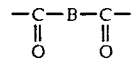

where B is a single bond, $C_6$-$C_{20}$ aryl or a $C_1$-$C_{20}$ alkyl, and those conforming to

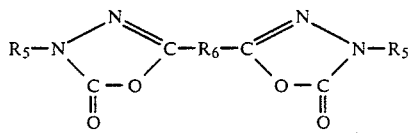

wherein
$R_5$ independently denotes a $C_1$-$C_8$ alkyl, $C_7$-$C_{18}$ alkaryl, a hydrogen atom or an alkali metal, or

where B is a $C_1$-$C_{18}$ alkyl or a $C_6$-$C_{16}$ aryl, or

where A is a $C_1$-$C_{12}$ alkyl or a $C_6$-$C_{16}$ aryl and $R_6$ a single bond, a $C_1$-$C_{12}$ alkyl or $C_6$-$C_{16}$ aryl.

* * * * *